United States Patent
Griffey et al.

(10) Patent No.: US 8,702,711 B2
(45) Date of Patent: Apr. 22, 2014

(54) REDUCED PRESSURE AUGMENTATION OF MICROFRACTURE PROCEDURES FOR CARTILAGE REPAIR

(75) Inventors: Edward S. Griffey, Fair Oaks Ranch, TX (US); Christopher Guy Coward, Wareham (GB); Colin John Hall, Poole (GB)

(73) Assignee: KCI Licensing, Inc., San Antonio, TX (US)

(*) Notice: Subject to any disclaimer, the term of this patent is extended or adjusted under 35 U.S.C. 154(b) by 627 days.

(21) Appl. No.: 12/643,508

(22) Filed: Dec. 21, 2009

(65) Prior Publication Data

US 2010/0168746 A1  Jul. 1, 2010

Related U.S. Application Data

(60) Provisional application No. 61/141,593, filed on Dec. 30, 2008.

(51) Int. Cl.
| | |
|---|---|
| *A61F 2/46* | (2006.01) |
| *A61B 17/58* | (2006.01) |
| *A61B 17/60* | (2006.01) |
| *A61F 2/00* | (2006.01) |

(52) U.S. Cl.
USPC .................. 606/86 R; 606/105; 604/101.01

(58) Field of Classification Search
USPC .......... 604/101.01–101.03; 606/86 R, 92–94, 606/105; 623/17.12; 424/422–428
See application file for complete search history.

(56) References Cited

U.S. PATENT DOCUMENTS

| | | | |
|---|---|---|---|
| 1,355,846 | A | 10/1920 | Rannells |
| 2,547,758 | A | 4/1951 | Keeling |
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |
| 3,367,332 | A | 2/1968 | Groves |
| 3,520,300 | A | 7/1970 | Flower, Jr. |
| 3,568,675 | A | 3/1971 | Harvey |
| 3,648,692 | A | 3/1972 | Wheeler |
| 3,682,180 | A | 8/1972 | McFarlane |
| 3,826,254 | A | 7/1974 | Mellor |

(Continued)

FOREIGN PATENT DOCUMENTS

| | | |
|---|---|---|
| AU | 550575 A1 | 8/1982 |
| AU | 745271 | 4/1999 |

(Continued)

OTHER PUBLICATIONS

International Preliminary Report on Patentability issued Jul. 5, 2011 for PCT/US2009/069031.

(Continued)

*Primary Examiner* — Andrew Yang
*Assistant Examiner* — Diana S Jones

(57) ABSTRACT

A system for applying a treatment to a defect in one bone of two bones forming a joint that comprises a bladder for delivering a reduced pressure to the defect and for providing a positive pressure as bracing between the two bones of the joint is disclosed. A method for applying such treatment is also disclosed. A bladder for applying such treatment that comprises a reduced-pressure chamber and a bracing chamber is also disclosed.

46 Claims, 8 Drawing Sheets

(56) References Cited

U.S. PATENT DOCUMENTS

| | | |
|---|---|---|
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,053,050 A | 10/1991 | Itay |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 5,677,355 A * | 10/1997 | Shalaby et al. ............... 521/61 |
| 5,723,331 A | 3/1998 | Tubo et al. |
| 5,786,219 A | 7/1998 | Zhang et al. |
| 5,811,094 A | 9/1998 | Caplan et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,491,693 B1 | 12/2002 | Lytinas |
| 6,493,568 B1 | 12/2002 | Bell et al. |
| 6,553,998 B2 | 4/2003 | Heaton et al. |
| 6,695,823 B1 | 2/2004 | Lina et al. |
| 6,727,224 B1 | 4/2004 | Zhang et al. |
| 6,763,836 B2 | 7/2004 | Tasto et al. |
| 6,767,334 B1 | 7/2004 | Randolph |
| 6,814,079 B2 | 11/2004 | Heaton et al. |
| 6,840,962 B1 | 1/2005 | Vacanti et al. |
| 6,856,821 B2 | 2/2005 | Johnson |
| 6,936,037 B2 | 8/2005 | Bubb et al. |
| 6,944,702 B1 | 9/2005 | Chilton et al. |
| 6,949,525 B2 | 9/2005 | Hermida |
| 6,951,553 B2 | 10/2005 | Bubb et al. |
| 6,958,149 B2 | 10/2005 | Vukicevic et al. |
| 6,982,298 B2 | 1/2006 | Calabro et al. |
| 7,004,915 B2 | 2/2006 | Boynton et al. |
| 7,070,584 B2 | 7/2006 | Johnson et al. |
| 7,077,832 B2 | 7/2006 | Fleischmann |
| 7,108,683 B2 | 9/2006 | Zamirowski |
| 7,169,151 B1 | 1/2007 | Lytinas |
| 7,186,224 B2 | 3/2007 | Windheuser |
| 7,214,202 B1 | 5/2007 | Vogel et al. |
| 7,279,612 B1 | 10/2007 | Heaton et al. |
| 7,316,672 B1 | 1/2008 | Hunt et al. |
| 7,346,945 B2 | 3/2008 | Phillips et al. |
| 7,351,250 B2 | 4/2008 | Zamierowski |
| 7,468,192 B2 | 12/2008 | Mizuno et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2003/0225347 A1 | 12/2003 | Argenta et al. |
| 2004/0134502 A1 | 7/2004 | Mizuno et al. |
| 2004/0225296 A1 | 11/2004 | Reiss et al. |
| 2006/0036331 A1 | 2/2006 | Lu et al. |
| 2006/0154367 A1 | 7/2006 | Kihm et al. |
| 2007/0021697 A1 | 1/2007 | Ginther et al. |
| 2007/0021698 A1 | 1/2007 | Fleischmann |
| 2007/0123895 A1 | 5/2007 | Lytinas |
| 2007/0185426 A1 | 8/2007 | Ambrosio |
| 2008/0033324 A1 | 2/2008 | Cornet et al. |
| 2008/0269674 A1 | 10/2008 | Stone |
| 2008/0275409 A1 | 11/2008 | Kane et al. |
| 2009/0005796 A1 | 1/2009 | Swain |
| 2010/0262092 A1 * | 10/2010 | Hartwell ............... 604/304 |

FOREIGN PATENT DOCUMENTS

| | | |
|---|---|---|
| AU | 755496 | 2/2002 |
| CA | 2005436 | 6/1990 |
| CA | 2216752 C | 7/2002 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| EP | 1466633 A1 | 10/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |

(56) References Cited

FOREIGN PATENT DOCUMENTS

| | | |
|---|---|---|
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 96/05873 | 2/1996 |
| WO | WO 97/18007 | 5/1997 |
| WO | WO 98/46164 A1 | 10/1998 |
| WO | WO 98/53768 A1 | 12/1998 |
| WO | WO 99/13793 | 3/1999 |
| WO | WO 00/38755 A2 | 7/2000 |
| WO | WO 00/59424 | 10/2000 |
| WO | WO 00/61206 A1 | 10/2000 |
| WO | WO 03/018098 A2 | 3/2003 |
| WO | WO 03/092620 A2 | 11/2003 |
| WO | WO 2004/060148 A2 | 7/2004 |
| WO | WO 2004/105576 A2 | 12/2004 |
| WO | WO 2005/009488 A2 | 2/2005 |
| WO | WO 2005/033273 A2 | 4/2005 |
| WO | WO 2007/067685 A2 | 6/2007 |
| WO | WO 2007/092397 A2 | 8/2007 |
| WO | WO 2007/106589 A2 | 9/2007 |
| WO | WO 2007/106590 A2 | 9/2007 |
| WO | WO 2007/106591 A2 | 9/2007 |
| WO | WO 2007/106592 A2 | 9/2007 |
| WO | WO 2007/106594 A2 | 9/2007 |
| WO | WO 2007/107330 | 9/2007 |
| WO | WO 2007/133555 A2 | 11/2007 |
| WO | WO 2007/133556 A2 | 11/2007 |
| WO | WO 2007/143060 A2 | 12/2007 |
| WO | WO 2008/013896 A2 | 1/2008 |
| WO | WO 2008/036162 A2 | 3/2008 |
| WO | WO 2008/036359 A2 | 3/2008 |
| WO | WO 2008-036361 A2 | 3/2008 |
| WO | WO 2008/042481 A2 | 4/2008 |
| WO | WO 2009/006226 A | 1/2009 |

OTHER PUBLICATIONS

N.A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986);pp. 94-96 (certified translation).

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.

G. Živadinović, V. Đukić, Ž. . Maksimović, Đ. . Radak, and P. Peška, "Vacuum Therapy in the Treatment of Peripheral Blood Vessels," *Timok Medical Journal* 11 (1986), pp. 161-164 (certified translation).

F.E. Johnson, "An Improved Technique for Skin Graft Placement Using a Suction Drain," *Surgery, Gynecology, and Obstetrics* 159 (1984), pp. 584-585.

A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," *British Journal of Surgery* 73 (1986), pp. 369-370.

D.E. Tribble, An Improved Sump Drain-Irrigation Device of Simple Construction, *Archives of Surgery* 105 (1972) pp. 511-513.

M.J. Morykwas, L.C. Argenta, E.I. Shelton-Brown, and W. McGuirt, "Vacuum-Assisted Closure: A New Method for Wound Control and

(56) References Cited

OTHER PUBLICATIONS

Treatment: Animal Studies and Basic Foundation," *Annals of Plastic Surgery* 38 (1997), pp. 553-562 (Morykwas I).

C.E. Tennants, "The Use of Hypermia in the Postoperative Treatment of Lesions of the Extremities and Thorax, "*Journal of the American Medical Association* 64 (1915), pp. 1548-1549.

Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians (Jul. 2007).

International Search Report and Written Opinion date mailed Aug. 16, 2010 for PCT Application No. PCT/US2009/069031.

Restriction Requirement date mailed Aug. 12, 2011 for U.S. Appl. No. 12/491,445.

Response filed Sep. 8, 2011 for U.S. Appl. No. 12/491,445.

Gould and Auchincloss. Immunology Today 20(2):77-82, 1999.

Azimzadeh et al. Hematology and Cell Therapy 38(4):331-343, 1997.

Non-Final Office Action date mailed Nov. 2, 2011 for U.S. Appl. No. 13/108,796.

International Search Report and Written Opinion date mailed May 6, 2010 for PCT Application No. PCT/US2009/048628.

\* cited by examiner

REDUCED PRESSURE AUGMENTATION OF MICROFRACTURE PROCEDURES FOR CARTILAGE REPAIR

CROSS-REFERENCE TO RELATED APPLICATIONS

This application claims the benefit of U.S. Provisional Application No. 61/141,593, filed Dec. 30, 2008, which is hereby incorporated by reference.

BACKGROUND

1. Field of the Invention

The present application relates generally to tissue treatment systems and in particular to treatment of articular cartilage undergoing microfracture procedure.

2. Description of Related Art

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment provides a number of benefits, including faster healing and increased formulation of granulation tissue. Typically, reduced pressure is applied to tissue through a porous pad or other manifolding device. The porous pad contains cells or pores that are capable of distributing reduced pressure to the tissue and channeling fluids that are drawn from the tissue. The porous pad often is incorporated into a dressing having other components that facilitate treatment.

Articular cartilage is a highly organized avascular tissue composed of chondrocytes formed in an extracellular matrix. This tissue is extremely important to the normal, healthy function and articulation of joints. Articular cartilage enables joint motion surfaces to articulate smoothly with a very low coefficient of friction. It also acts as a cushion to absorb compressive, tensile, and shearing forces and, thus, helps protect the ends of bone and surrounding tissue.

Age, injury and wear, and cartilage disorders, such as osteoarthritis, affect millions of people throughout the world. Traumatic chondral injuries, for example, are common in sports and other activities that cause severe stress and strain to joints. Osteoarthritis is also a common condition that develops as cartilage wears, weakens, and deteriorates at the joint motion surfaces of bones. Indeed, it is currently believed that 85% of all Americans will develop degenerative joint disease as a result of normal activities that damage articular cartilage.

Articular cartilage is generally thin with an extremely low or insignificant blood flow and, as such, has a very limited ability to repair or heal itself. Partial-thickness chondral defects, for example, cannot spontaneously heal. If these defects are left untreated, they often degenerate at the articular surface and progress to osteoarthritis. Full-thickness defects that penetrate subchondral bone can undergo some spontaneous repair if fibrocartilage forms at the defect. Even in spite of the formation of fibrocartilage, clinical evidence shows that full-thickness defects continue to degenerate and progress to osteoarthritis if these defects are left untreated.

Early diagnosis and treatment are crucial to hindering or stopping the progression of arthritis and degeneration of articular cartilage at joint motion surfaces. Today, depending on the grade of chondral damage, patients usually have several surgical options to repair or regenerate articular cartilage. Some current techniques to repair cartilage include implantation of chondrocytes, implantation of synthetic matrices and surgical intervention, with reattachment and reconstruction of the damaged tissue. None of these methods are totally satisfactory and they rarely restore full function or return the tissue to its native normal state. In addition, none of these methods are proven to regenerate cartilage in situ and in vivo.

Micro-fracture surgery is one treatment modality used to treat cartilage defects. This technique is a marrow-stimulating arthroscopic procedure to penetrate the subchondral bone to induce fibrin clot formation and the migration of primitive stem cells from the bone marrow into the defective cartilage location. Generally, the base of the defective area is shaved or scraped to induce bleeding. An arthroscopic awl or pick is then used to make small holes or microfractures in the subchondral bone plate. The end of the awl is manually struck with a mallet to form the holes while care is made not to penetrate too deeply and damage the subchondral plate. The holes penetrate a vascularisation zone and stimulate the formation of a fibrin clot containing pluripotential stem cells. The clot fills the defect and matures into fibrocartilage.

While microfracture surgery has a high success rate, patients cannot return to sports or other intense activities for about 4 months, even with the help of physical therapy. Additionally, the tissue that forms in the defect is primarily fibrocartilage (this constitutes a repair process whereby a different tissue type is formed), which does not have the same functional characteristics of articular (hyaline) cartilage. As such, there is currently an acute need for a method that leads to more of a regenerative response (forms the same type of tissue that was damages, for example, hyaline cartilage) rather than a repair response and that reduces the overall time of healing.

It would therefore be advantageous to provide devices, methods and systems to promote healing and/or tissue regeneration after microfracture surgery. Such devices, methods and systems would decrease healing time, and lead to better functional outcomes thus increasing the patient's quality of life and enable a more rapid return to normal daily activities.

SUMMARY

The problems presented by existing methods for microfracture surgery are solved by the systems and methods of the illustrative embodiments described herein. These systems and methods are designed to deliver reduced pressure to the joint space where microfracture surgery is performed. Traditional reduced pressure delivery methods to a joint space, in particular a knee joint, would apply reduced pressure to the entire joint. The systems and methods described herein concentrate application of the reduced pressure on the defect (e.g., the site of the microfracture surgery) by utilizing a bladder having a reduced-pressure chamber with an opening that surrounds the defect to avoid applying reduced pressure to the entire joint.

In one embodiment, a system for applying a treatment to a defect in a first bone of two bones forming a joint is disclosed and comprises a reduced-pressure source for providing a reduced pressure, a positive-pressure source for providing a positive pressure, and a bladder. The bladder is formed with a reduced-pressure chamber in fluid communication with the reduced-pressure source and a bracing chamber in fluid communication with the positive-pressure source. The reduced-pressure chamber and bracing chamber both have walls formed from a flexible material, and the reduced-pressure chamber has an opening sized to substantially surround the defect in the first bone. A portion of the walls of each of the reduced-pressure chamber and the bracing chamber form an interior wall of the bladder.

The system further comprises a manifold positioned within the reduced-pressure chamber between the interior wall and the opening in the reduced-pressure chamber and formed of a porous material for distributing reduced pressure and providing structural support between the first bone and contact portion of the interior wall. When positive pressure is applied to the bracing chamber, the walls of the bracing chamber inflate to provide bracing between the interior wall and a second bone of the two bones. When reduced pressure is applied to the reduced-pressure chamber, the walls of the reduced-pressure collapse toward the interior wall causing the manifold to provide a seal with the contact portion of the interior wall against the defect and provide bracing between the contact portion of the interior wall and the first bone.

In another embodiment, a method for applying the treatment is also disclosed and first comprises performing surgery on the defect in the first bone. The method then comprises positioning a reduced-pressure chamber in the joint adjacent the defect, positioning a bracing chamber in the joint between the reduced-pressure chamber and a second bone of the two bones, and positioning a manifold within the reduced-pressure chamber adjacent the defect and the bracing chamber. The method further comprises applying a positive pressure to the bracing chamber to force the manifold against the first bone to brace the reduced-pressure chamber against a second bone of the two bones and then applying a reduced-pressure to the defect through a hole in the reduced-pressure chamber and the manifold, In a further embodiment, a method is provided that includes performing microfracture surgery to a knee. The method comprises creating at least one microfracture in a bone at the base of an articular cartilage defect in the knee, then applying reduced pressure to the site of the defect.

Other objects, features, and advantages of the illustrative embodiments will become apparent with reference to the drawings and detailed description that follow.

DETAILED DESCRIPTION OF ILLUSTRATIVE EMBODIMENTS

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1A:
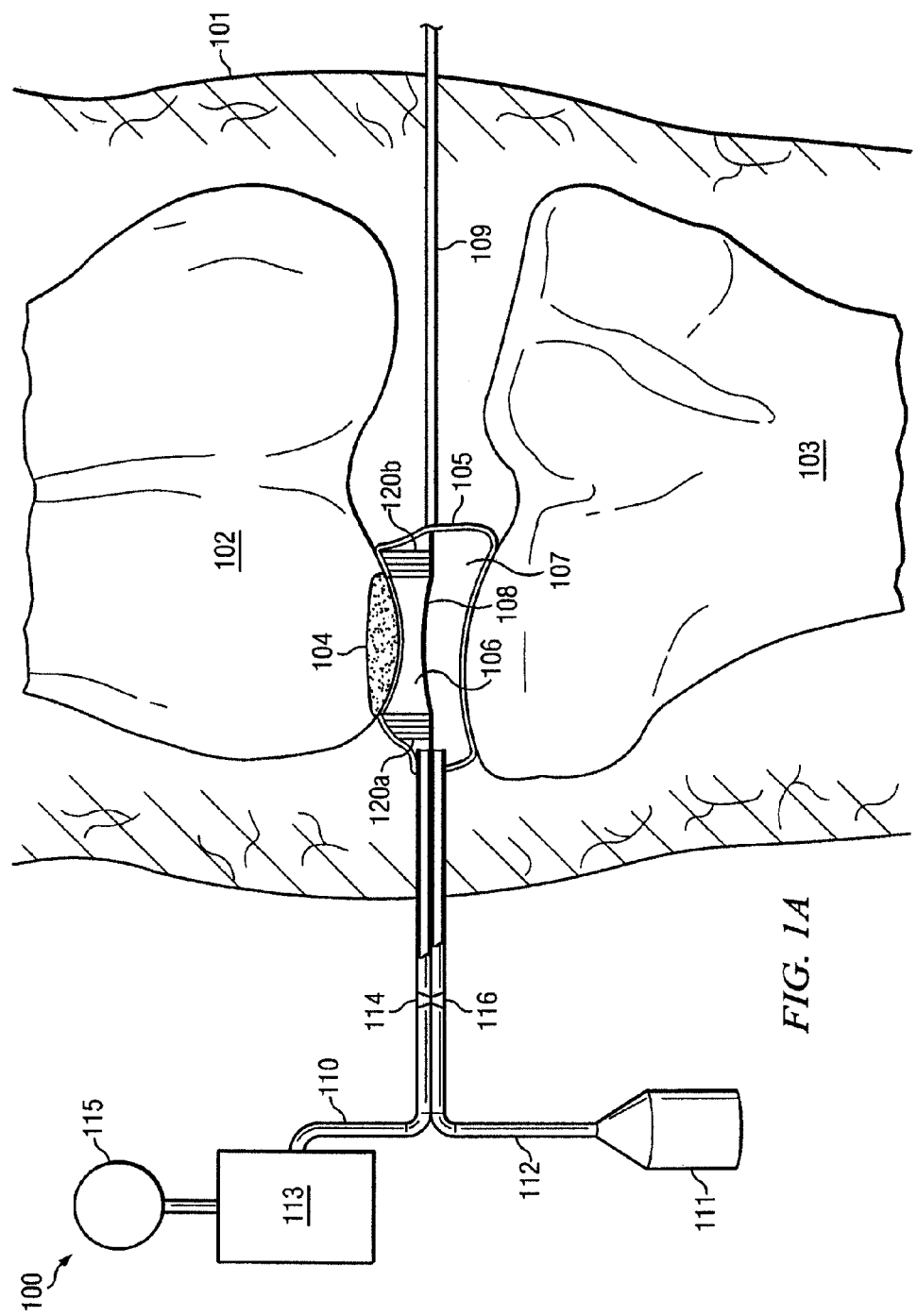
FIG. 1A is a schematic, cross-sectional view of a reduced-pressure treatment system for repairing cartilage in a knee joint that includes a fluidic system, a bladder positioned between the femur and tibia of the knee joint, and a first embodiment of a manifold structure within the bladder.
Figure 1B:
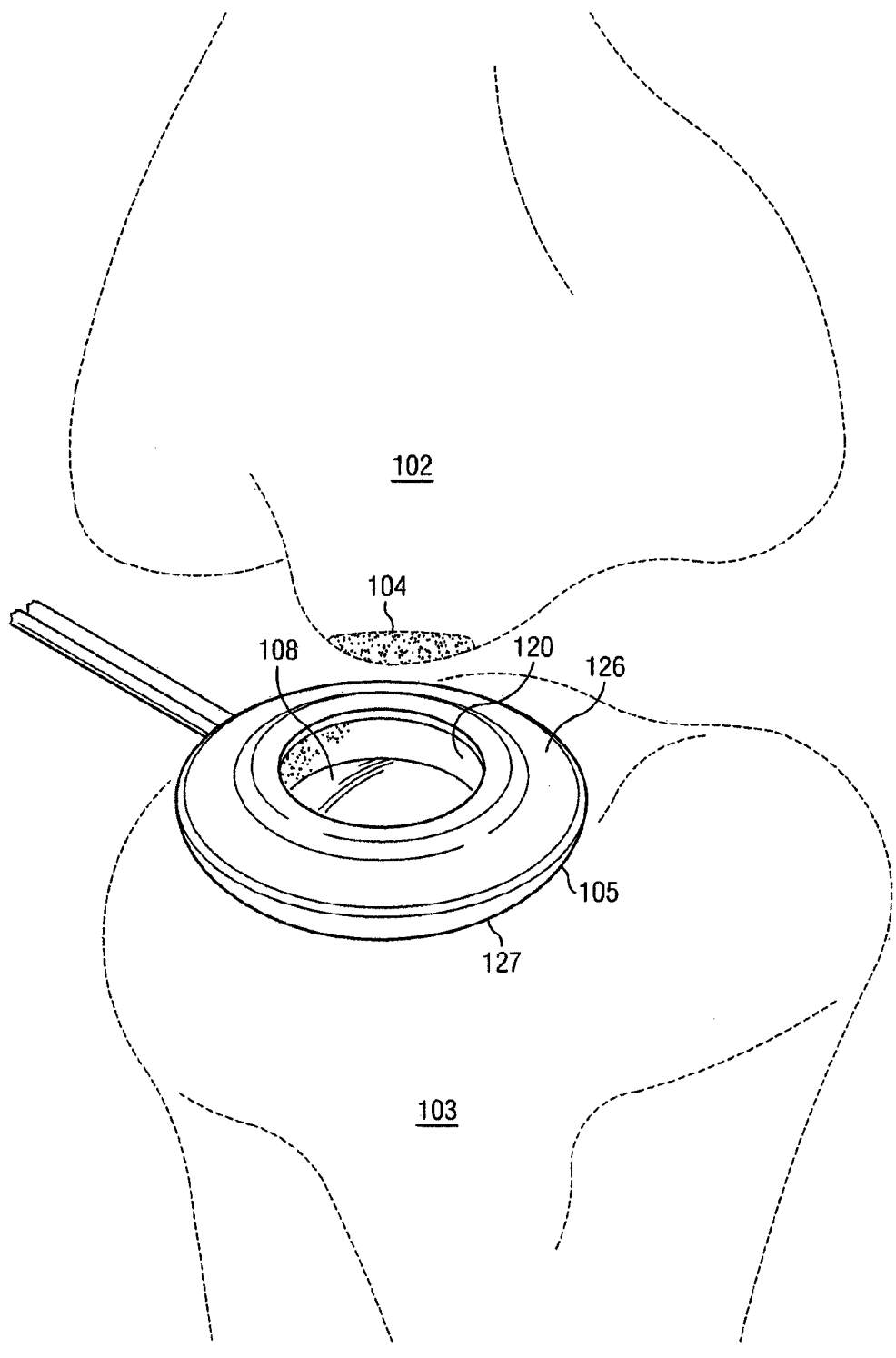
FIG. 1B is a schematic, perspective view of the bladder and femur shown in FIG. 1A.

Referring to FIGS. 1A and 1B, a reduced pressure therapy system 100 for applying reduced pressure and facilitating the growth of tissue at a tissue site in the body of a patient such as, for example, the knee joint in a leg 101 of the patient comprising the femur 102 and tibia 103. Any portion of the knee joint may have developed a defect that needs repair, for example, a defect 104 in the articular cartilage of the lateral condyle of the femur 102. The defect 104 may also be a micro-fracture surgery site as described above where it is desired to regenerate, repair, add or promote growth of new cartilage tissue or any tissue functioning as a structure and support of the body including, without limitation, areola connective tissue, dense connective tissue and cartilage.

The reduced pressure therapy system 100 also comprises a reduced pressure source 115 for providing a reduced pressure to a bladder 105 comprising a reduced-pressure chamber 106 and a bracing chamber 107 divided by an interior wall 108 within the bladder 105. It should be understood that the chambers 106, 107 may be separate chambers without the common interior wall 108. The bladder 105 is positioned between the bones 102, 103 with the reduced-pressure chamber 106 positioned adjacent the femur 102. It should be understood that the defect 104 could also be in the tibia 103 with the reduced-pressure chamber 106 positioned adjacent such defect in the tibia 103. The reduced pressure source 115 is fluidly coupled to the reduced-pressure chamber 106 of the bladder 105 via a first conduit 110. The reduced pressure therapy system 100 further comprises a canister 113 fluidly coupled between the reduced pressure source 115 and the reduced pressure chamber 106 of the bladder 105 to collect bodily fluids, such as blood or exudate, that are drawn from the femur 102 via the defect 104. In one embodiment the reduced-pressure source 115 and the canister 113 are integrated into a single housing structure.

In the context of this specification, the term "reduced pressure" generally refers to a pressure that is less than the ambient pressure at a tissue site that is subjected to treatment. In most cases, this reduced pressure will be less than the atmospheric pressure of the location at which the patient is located. Although the terms "vacuum" and "negative pressure" may be used to describe the pressure applied to the tissue site, the actual pressure applied to the tissue site may be significantly greater than the pressure normally associated with a complete vacuum. Consistent with this nomenclature, an increase in reduced pressure or vacuum pressure refers to a relative reduction of absolute pressure, while a decrease in reduced pressure or vacuum pressure refers to a relative increase of absolute pressure.

The system 100 further comprises a first fluid supply 111 that is fluidly coupled to the bracing chamber 107 of the bladder 105 via a second conduit 112. The first fluid supply 111 provides a bracing substance to the bracing chamber 107 via the second conduit 112 to fill the bracing chamber 107 under a positive pressure so that the bracing chamber 107 expands and exerts a positive force on the tibia 103 and surrounding tissue as well as the interior wall 108 of the bladder 105. The positive pressure applied to the bracing substance in the bracing chamber 107 is sufficient to allow the bracing chamber 107 to conform to the shape and contours of the tibia 103 and surrounding tissue while simultaneously providing a cushion between the femur 102 and the tibia 103 without collapsing. It is to be understood that the bracing chamber 107 of the bladder 105 may comprise multiple chambers to achieve the desired cushioning and conformance with the tibia 103 and surrounding tissue. The bracing substance may be a gas or a liquid such as, for example, a highly viscous compressible material such as a putty, slurry, or colloid.

Both the first conduit 110 and the second conduit 112 may be coupled to the bladder 105 via connectors 114 and 116, respectively. Both conduits 110, 112 may be coated with an anti-coagulant to prevent a build-up of bodily fluids or blood within the conduits. As used herein, the term "coupled" includes direct coupling or indirect coupling via a separate object. The term "coupled" also encompasses two or more components that are continuous with one another by virtue of each of the components formed from the same piece of material. Also, the term "coupled" may include chemical, mechanical, thermal, or electrical coupling. Fluid coupling means that fluid is in communication between the designated parts or locations.

Figure 2A:
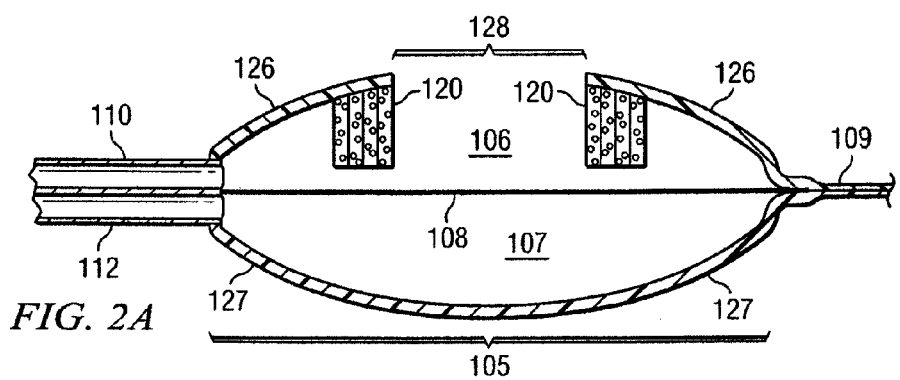
FIGS. 2A and 2B are schematic, cross-sectional views of the bladder shown in FIG. 1A with and without reduced pressure being applied to the bladder.
Figure 2B:
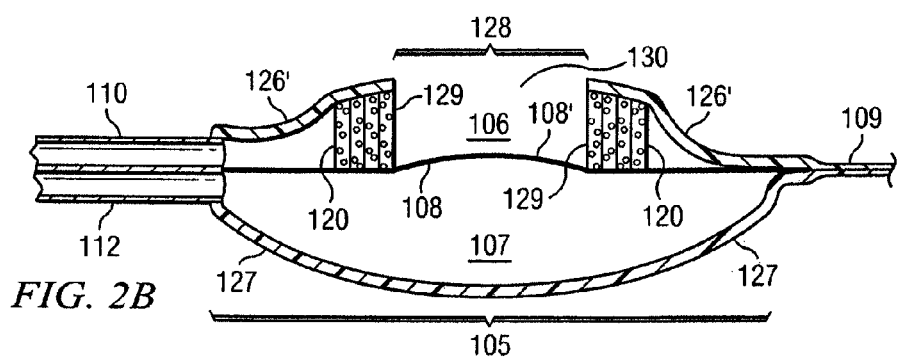

The bladder 105 is shown with and without a reduced pressure applied to the reduced-pressure chamber 106 in FIGS. 2B and 2A, respectively. Referring more specifically to FIG. 2A, the bladder 105 comprises two exterior walls including a reduced-pressure exterior wall 126 which forms the external surface of the reduced-pressure chamber 106 and bracing exterior wall 127 which forms the external wall of the bracing chamber 107. The reduced-pressure exterior wall 126 has a generally circular opening 128 which is shaped to fit the perimeter of the defect 104. The bladder 105 further comprises a manifold structure 120 that may be two separate manifold components 120a, 120b positioned on both sides of the defect 104 in the femur 102 as shown in FIG. 1A or that may be substantially cylindrical in shape with an inner diameter that is concentrically aligned with the opening 128 of the reduced-pressure exterior wall 126 as shown in FIG. 1B. The upper surface of the manifold structure 120 may be sealed against the inside surface of the reduced-pressure exterior wall 126. The manifold structure 120 may have a height somewhat less than the distance between the reduced-pressure exterior wall 126 and the interior wall 108 so that it is slightly suspended over the interior wall 108 when the reduced-pressure chamber 106 is not under pressure.

When a reduced pressure is applied to the reduced-pressure chamber 106 as shown in FIG. 2B, the reduced-pressure exterior wall 126 collapses to the position shown as 126' with the manifold structure 120 being forced against the interior wall 108 and forming a seal with a portion of the interior wall 108 to concentrate the reduced pressure on the defect 104. The portion of the interior wall 108 defined by the inner diameter of the manifold structure 120 may form a slightly dimpled portion 108' as a result of the reduced pressure being applied through the manifold structure 120. The dimpled portion 108' of the interior wall 108 and the inner surface 129 of the manifold structure 120 define a cavity 130 that is positioned adjacent the defect 104. Consequently, the reduced-pressure exterior wall 126 provides a seal around the defect 104 for applying the reduced pressure directly to the defect 104 via the opening 128 in the reduced-pressure exterior wall 126. The manifold structure 120 also serves to prevent the exterior wall 126 from collapsing against the interior wall 108, allowing the reduced pressure to continue to be applied to the defect 104 in the femur 102. The manifold structure 120, whether a single piece or multiple manifold components 120a and 120b, is selected to provide adequate structural support within the reduced-pressure chamber 106 between the femur 102 and the interior wall 108 while still functioning within the reduced-pressure chamber 106 as forming a part of the cavity 130.

The interior wall 108 is substantially impermeable to block the transmission of fluids including both liquids and gases. The interior wall 108 may be a single layer of material or multiple layers of material depending on the manufacturing process of the bladder 105. Although the manifold structure 120 may form a slight dimpled portion 108' as a result of the reduced pressure being applied to the reduced pressure chamber 106 and the positive pressure being applied to the bracing chamber 107, the interior wall 108 is substantially inflexible to reduce the amount of bending or flexing in response to the pressures being applied on both sides. Such materials may include, for example, fiberglass, metals, rubbers, or plastics alone or in combination. The interior wall 108 must be sufficiently inflexible or rigid to ensure that the cavity 130 does not collapse against the defect 104 when the reduced pressure and bracing pressure are applied to the bladder 105.

The exterior walls 126, 127 are also fabricated from an impermeable material to substantially block the transmission of fluids. Additionally, the exterior walls 126, 127 must be sufficiently thick to withstand the tensile stress and compressive stress created by the application of the reduced pressure to the reduced-pressure chamber 106 and the positive pressure to the bracing chamber 107, respectively. Consequently, the exterior walls 126, 127 may be formed of multiple layers of material having the same or different properties. For example, the exterior walls 126, 127 may have a first layer that is impermeable to fluids and second layer that has sufficient flexibility and structural support when under pressure. These characteristics are of course dependent upon the specific materials used to fabricate the exterior walls 126, 127 of the bladder 105.

The material used to form the exterior walls 126, 127 may contain one or more elastomers so that they have rubber-like properties. For example, in some embodiments, the flexible material has elongation rates greater than 100% and a significant amount of resilience. The resilience of a material refers to the material's ability to recover from an elastic deformation. Examples of elastomers include, but are not limited to, natural rubbers, polyisoprene, stryrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, and silicones. Elastomers may also include, but are not limited to, polyurethane elastomers, including elastomers based on both aromatic and aliphatic isocyanates; flexible polyolefins, including flexible polyethylene and polypropylene homopolymers and copolymers; styrenic thermoplastic elastomers; polyamide elastomers; polyamide-ether elastomers; ester-ether or ester-ester elastomers; flexible ionomers; thermoplastic vulcanizates; flexible poly(vinyl chloride) homopolymers and copolymers; flexible acrylic polymers; and blends and alloys of these, such as poly(vinyl chloride) alloys like poly(vinyl chloride)-polyurethane alloys. The exterior walls 126, 127 may also include, but are not limited to, polyester-polyurethanes, polyether-polyurethanes, and polycarbonate-polyurethanes. The different elastomeric materials described above may be combined as lends to form the exterior walls 126, 127 in one layer, or alternatively, may be formed as separate layers. The exterior walls 126, 127 may be formed of bioinert materials, i.e., materials which do not elicit a strong immunological reaction against the material and are not toxic, but which do not degrade within the body over time.

The manifold structure 120 distributes the reduced pressure within the reduced-pressure chamber 106 to the defect 104 while providing support as a spacer between the interior wall 108 and the reduced-pressure exterior wall 126 in the collapsed position 126' as shown in FIG. 2B. When the reduced-pressure exterior wall 126 is forced against the femur 102, the reduced pressure is applied directly to the defect 104 via the cavity 130 which includes the manifold structure 120 that continues to distribute the reduced pressure to the defect 104. The manifold structure 120 comprises an open-cell foam material that includes a plurality of cells fluidly coupled to each other to form a plurality of flow channels within the manifold structure 120. The cells and flow channels may be of uniform shape and size or may include a pattern or random variations to more precisely direct the flow of fluids through the flow channels within the manifold structure 120.

In one illustrative embodiment, the manifold structure 120 is a foam material that may be either hydrophobic or hydrophilic. In one non-limiting example, the manifold structure 120 is an open-cell, reticulated polyurethane foam such as GranuFoam® dressing available from Kinetic Concepts, Inc. of San Antonio, Tex. In the example in which the manifold structure 120 is made from a hydrophilic material, the manifold structure 120 also functions to wick fluid out of the cavity 130, while continuing to provide reduced pressure to the defect 104 as a manifold. The wicking properties of the manifold structure 120 draw fluid away from the defect 104 by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

In another embodiment, the manifold structure 120 may be constructed from bioresorbable materials that do not have to be removed from a patient's body after the defect 104 has been repaired and the reduced-pressure chamber 106 fully collapses. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The manifold structure 120 may further serve as a scaffold for new cell-growth, or a scaffold material may be used in conjunction with the manifold structure 120 to promote cell-growth. A scaffold is a substance or structure used to enhance or promote the growth of cells or formation of tissue, such as a three-dimensional porous structure that provides a template for cell growth. Illustrative examples of scaffold materials include synthetic, biosynthetic, and biologic material such as calcium phosphate, collagen, PLA/PGA, coral hydroxy apatites, carbonates, autologous tissue, or processed allograft or xenograft materials.

The manifold structure 120 may also include a closed-cell material to provide sufficient support within the reduced-pressure chamber 106 to prevent the exterior wall 126 collapsing prematurely on the interior wall 108. The closed-cell material also contains a plurality of cells, but the majority of these cells are not fluidly coupled to each other with flow channels so that they provide a more solid structural support within the reduced-pressure chamber 106. The closed-cell material is sufficiently dense to maintain the three-dimensional shape of the manifold structure 120 to provide structural support within the reduced-pressure chamber 106 and to prevent the open-cells from collapsing and cutting off the flow of reduced pressure through the flow channels.

Consequently, the size of the cells in the manifold structure 120 must be sufficiently large to facilitate the communication of fluids through the plurality of cells in the manifold structure 120, but sufficiently small with lower porosities to provide structural support within the reduced-pressure chamber 106. While the size of the cells in the manifold structure 120 is not exactly known, it is between about 100 microns at the low end to maintain sufficient permeability allowing air and fluids to move therethrough when under pressure, and about 1500 microns on the high end to maintain sufficient structural support for the femur 102. Further, the size and number of cells in the manifold structure 120 affect the porosity of the manifold structure 120. In one embodiment, the porosity percentage should be at least about 50% to ensure that the manifold structure 120 continues to facilitate fluid flow through the open-cell structure. The porosity percentage should be no greater than about 85% to ensure that the manifold structure provides sufficient structural support. Thus, the porosity of the manifold structure 120 should be in a range of about 50% to about 85%.

Referring again to FIGS. 1A, 1B, and 2B, the interior wall 108 is sufficiently rigid to prevent the dimpled portion 108' of the interior wall 108 and the inner diameter surface 129 of the manifold structure 120 from contacting the defect 104. Material may be positioned within the cavity 130 adjacent the defect 104 that promotes healing of the defect 104, or provides additional structural support, or provides a barrier to isolate the reduced-pressure chamber 106 from the defect 104, or all the foregoing. For example, additional manifold material may be placed within the cavity 130 to provide additional structural support in a similar fashion as the manifold structure 120 described above, and/or to function as scaffold material to promote healing of the defect 104. A manifold structure may also function as a scaffold material to promote healing of the defect 104. Such a manifold structure may be bioresorbable and left in place after the reduced pressure delivery system 100 is removed.

Figure 3:
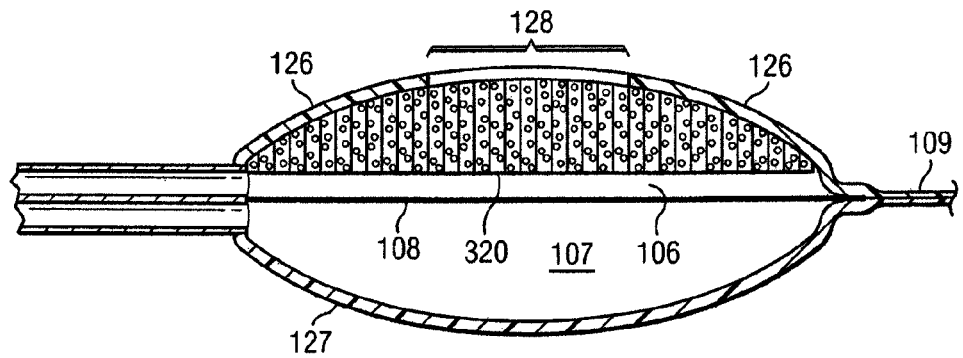
FIG. 3 is a schematic, cross-sectional view of the bladder shown in FIG. 1A including a second embodiment of a manifold structure.

The shape of the manifold structure 120 may be any that prevents the exterior wall 126 from collapsing against the interior wall 108 within the reduced-pressure chamber 106 when being subjected to a reduced pressure. Thus, the manifold structure 120 may support only a portion of the exterior wall 126 of the reduced-pressure chamber 106 as illustrated in FIG. 2A. Alternatively, a manifold structure 320 may fill most of the reduced-pressure chamber 106 to support the entire inner portion of the exterior wall 126 of the reduced-pressure chamber 106 as shown in FIG. 3. When a reduced pressure is applied to the reduced-pressure chamber 106, the reduced-pressure exterior wall 126 does not collapse to the position shown as 126' as shown in FIG. 2B. However, the manifold structure 320 is still forced against the interior wall 108 to form the cavity 130 positioned adjacent the defect 104. Consequently, the reduced-pressure exterior wall 126 provides a seal around the defect 104 for applying the reduced pressure directly to the defect 104 via the opening 128 in the reduced-pressure exterior wall 126 as shown in FIG. 2B. This particular embodiment provides more structural support to the reduced-pressure chamber 106 of the bladder 105 if, for example, more support is needed for the femur 102 as preferred in some embodiments.

Figure 4:
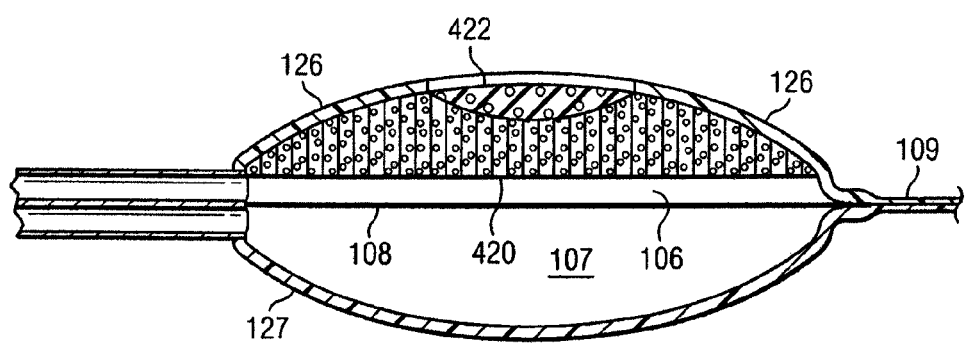
FIG. 4 is a schematic, cross-sectional view of the bladder shown in FIG. 1A including scaffold material.

The manifold structure 320 may also include a portion that functions as scaffold material to promote healing of the defect 104. The scaffold portion may be sized to fill a defect that is a gap or void in the femur 102 and may be a separate or integrated component of the manifold structure 320. The scaffold portion of the manifold structure 320 may be bioresorbable and left in place after reduced-pressure delivery system 10 is removed. Referring more specifically to FIG. 4, such a manifold structure 420 is shown that includes a scaffold component 422 to promote regeneration of the defect 104 while at the same time providing additional structural support between the femur 102 and the interior wall 108 of the bladder 105. The manifold structure 420 may be constructed of similar foam material as the manifold structure 120 as described above. The scaffold component 422 comprises primarily open-cell material to facilitate fluid communication between the manifold structure 420 and the defect 104. As such, the scaffold component 422 serves as an additional manifold to more efficiently distribute reduced pressure across the entire surface of the defect 104, while at the same time providing some cushion between the femur 102 and the interior wall 108 of the bladder 105. The scaffold component 422 of the manifold structure 420 may be coated or infused with growth factors, cells or nutrients to promote the growth of cells and/or the regeneration of cartilage tissue. The scaffold component 422 may also be self-seeded whereby the reduced pressure pulls cells from the surrounding bone or other body tissues into the cells of the scaffold component 422 where they may grow and/or form new tissue. Further, the scaffold component 422 may be seeded with cells ex vivo, prior to application.

The size of the cells in the scaffold component 422 must be sufficiently large to maintain fluid flow through the plurality of cells in the structure, but sufficiently small with lower porosities to provide enough structural support within the scaffold component 422 to ensure that the flow channels therein do not collapse significantly and the scaffold component 422 retains its shape to function as a scaffold when a reduced pressure is applied to the reduced-pressure chamber 106. The scaffold component 422 in a reduced pressure environment may have the open cell structure that collapses to about 10%, about 20%, about 40%, about 80%, or any range therebetween to avoid disrupting or significantly altering fluid communication within the scaffold component 422. The cell size and porosity of the scaffold component would be in the same range as described above for the manifold structure 120.

The scaffold component 422 may be constructed as a separate component that contacts a surface of the manifold structure 120 with a loose interface that allows the scaffold component 422 to separate easily from the manifold structure 120 when the bladder 105 is removed from the femur 102. Thus, the scaffold component 422 remains in place at the site of the repaired defect 104 when the bladder 105 is removed. Alternatively, the scaffold component 422 may be constructed so that it adheres to the surface of the manifold structure 120 using, for example, an adhesive that causes the scaffold component 422 to remain attached to the manifold structure 120 when the bladder 105 removed from the femur 102. Thus, the scaffold component 422 does not remain in place at the site of the repaired defect 104 when the bladder 105 is removed. When the scaffold component 422 is intended to be removed with the manifold structure 420, they may be fabricated as a unitary component (not shown) with dual porosities such that they function in the same manner as described above. Such unitary components with dual porosities are disclosed and described in U.S. Pat. No. 6,695,823 and International Application No. PCT/US2008/000596 (International Publication No. WO 2008/091521 A2), both of which are hereby incorporated by reference herein.

The scaffold component 422 may be constructed from materials including synthetics, biosynthetics, or biologics such as calcium phosphate, collagen, PLA/PGA, coral hydroxy apatites, carbonates, autologous tissue, or processed allograft or xenograft materials. The scaffold component 422 may also be formed of bioinert materials, i.e., materials which do not elicit a strong immunological reaction against the material nor are toxic, but which do not degrade within the body over time. In another embodiment, the scaffold component 422 is formed of biocompatible materials, i.e., materials which do not elicit a strong immunological reaction against the material nor are toxic, and which degrade into non-toxic, non-immunogenic chemical species which are removed from the body by excretion or metabolism. In yet another embodiment, the scaffold component 422 is formed of biodegradable materials, i.e., materials which are enzymatically or chemically degraded in vivo into simpler chemical species.

In some embodiments, the scaffold component 422 is made of biocompatible and/or biodegradable materials. Thus, the scaffold component 422 may remain at the site of the defect 104 even if the bladder 105 is removed from the knee joint. When the scaffold component 422 remains in the knee joint, it should be constructed of materials having appropriate dimensions for the site and sufficient strength to support new tissue growth. The biocompatible and/or biodegradable materials may include, but is not limited to, lactide, poly(lactide) (PLA), glycolide polymers, poly(glycolic acid) (PGA), poly (lactide-co-glycolide) (PLGA), ethylene glycol/lactide copolymers, polycaprolactone, poly (p-dioxanone), polyhydroxybutyrate, polyurethanes, polyphosphazenes, poly(ethylene glycol)-poly(lactide-co-glycolide) co-polymer, polyhydroxyacids, polycarbonates, polyamides, polyanhydrides, polyamino acids, polyortho esters, polyacetals, degradable polycyanoacrylates, polycarbonates, polyfumarates, degradable polyurethanes, proteins such as albumin, collagen, fibrin, synthetic and natural polyamino acids, polysaccharides such as alginate, heparin, other naturally occurring biodegradable polymers of sugar units, processed cadaveric or non-human tissues including but not limited to dermis, pericardium, tendon, or cartilage.

If the scaffold component 422 is made of biocompatible and/or biodegradable materials, the materials may be designed to degrade within a desired time frame. In one embodiment, the desired degradation time frame is one to two weeks. In another embodiment, the desired degradation time frame is between one month and one year. In yet another embodiment, the desired degradation time is greater than a year. Further, in some embodiments, scaffold component 422 made of biocompatible or biodegradable materials may degrade in a manner related to the molecular weights of the materials used to make the scaffold component 422. Thus, a higher molecular weight material may result in scaffold component 422 that retains its structural integrity for longer periods of time, while lower molecular weights result in faster degradation with shorter scaffold life.

Figure 5:
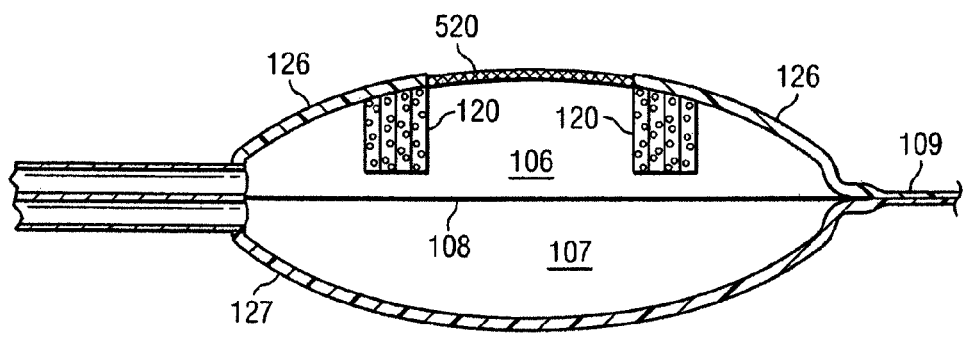
FIG. 5 is a schematic, cross-sectional view of the bladder shown in FIG. 1A including a barrier material.

As indicated above, the cavity 130 may include a material positioned within the void adjacent the defect 104 that promotes healing of the defect 104, provides additional structural support, and provides a barrier to isolate the reduced-pressure chamber 106 from the defect 104. FIG. 5 illustrates another embodiment of the reduced-pressure chamber 106 comprising a barrier material 520 that covers the opening in the exterior wall 126 and closes the cavity 130. The barrier material 520 may be attached to the manifold structure 120 and/or attached to the exterior wall 126 of the reduced-pressure chamber 106. Thus, the barrier material 520 directly contacts the surface of the defect 104 when the cavity 130 is placed adjacent the defect 104.

The barrier material 520 may comprise one or more pieces of material that covers a portion, or all, of the exterior wall 126 of the reduced-pressure chamber 106. The barrier material 520 is preferably fabricated from a material that allows the reduced-pressure chamber 106 to be in fluid communication with the defect 104 while isolating the defect 104 from direct communication with the cavity 130. As such, the barrier material 520 may be, for example, a mesh, sieve, a screen, or a solid sheet with spaces or a punched pattern. The barrier material 520 may have sufficient strength to provide additional structural support for the knee joint.

Figure 6:
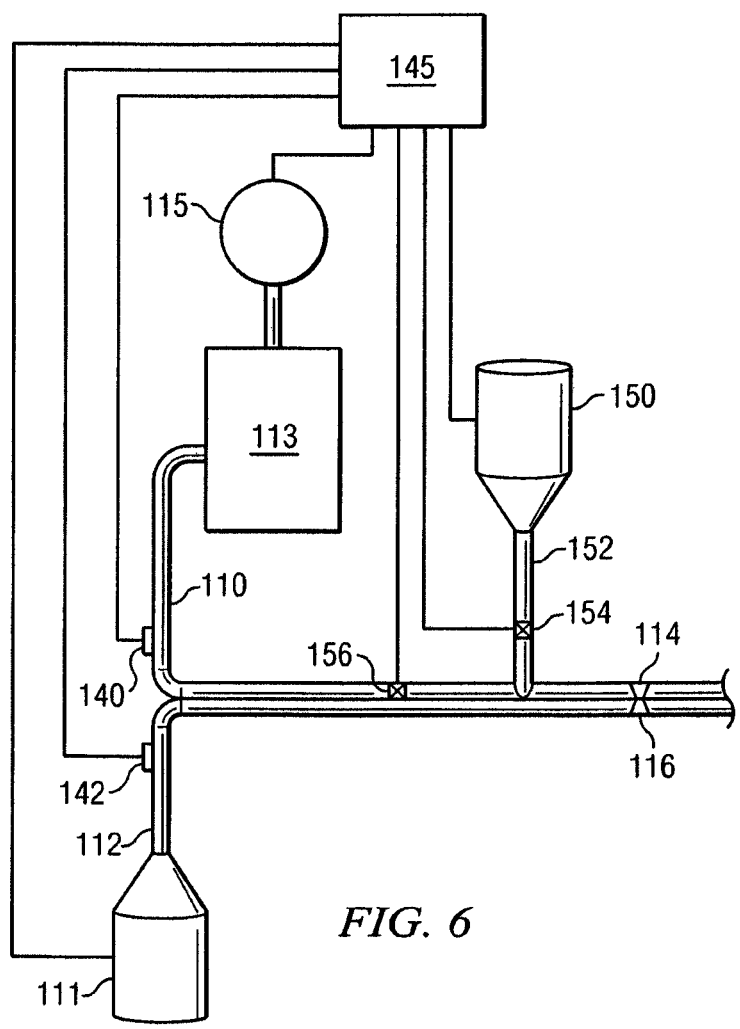
FIG. 6 is a schematic view of a fluid control system for the fluidic system shown in FIG. 1A.

Referring to FIG. 6, the reduced pressure therapy system 100 may further comprise pressure sensors 140, 142 operably connected to the first and second conduits 110, 112 to measure the reduced pressure and the bracing pressure, respectively. The system further includes a control unit 145 electrically connected to the pressure sensors 140, 142, the reduced pressure source 115, and the first fluid supply 111 that provides the bracing fluids through the second conduit 112 to the bracing chamber 107. The pressure sensor 140 measures the reduced pressure of the reduced-pressure chamber 106, and also may indicate whether the first conduit 110 is occluded with blood or other bodily fluids. The pressure sensor 140 also provides feedback to control unit 145 which regulates the reduced-pressure therapy being applied by the reduced-pressure source 115 through the first conduit 110 to the reduced-pressure chamber 106. Correspondingly, the pressure sensor 142 measures the positive pressure of the bracing fluid being applied by the first fluid supply 111 through the second conduit 112 to the bracing chamber 107. The pressure sensor 142 also provides feedback to the control unit 145 which regulates positive pressure therapy being applied by the reduced-pressure source 115 to the bracing chamber 107. The control unit 145 also balances the relative amount of reduced pressure and positive pressure being applied to the reduced-pressure chamber 106 and the bracing chamber 107, respectively, so that sufficient pressures are being applied to both the femur 102 and the tibia 103, respectively, and the interior wall 108 as described above.

The reduced-pressure therapy system 100 may also comprise a second fluid supply 150 fluidly coupled to the first conduit 110 via third conduit 152 and operatively connected to the control unit 145. The second fluid supply 150 may be used to deliver growth and/or healing agents to the defect 104 including, without limitation, an antibacterial agent, an antiviral agent, a cell-growth promotion agent, an irrigation fluid, or other chemically active agents. The system 100 further comprises a first valve 154 positioned in the third conduit 152 to control the flow of fluid therethrough, and a second valve 156 positioned in the first conduit 110 between the reduced-pressure source 115 and the juncture between the first conduit 110 and the third conduit 152 to control the flow of reduced pressure. The control unit 145 is electrically connected to the second fluid supply 150 and the first and second valves 154, 156 to control the delivery of reduced pressure and/or fluid from the second fluid supply 150 to the reduced-pressure chamber 106 as required by the particular therapy being administered to the patient. The second fluid supply 150 may deliver the liquids as indicated above, but may also deliver air to the reduced-pressure chamber 106 to promote healing and facilitate drainage at the site of the defect 104.

The independent paths of fluid communication provided by the conduits 110, 112, and 152 may be accomplished in a number of different ways, including that of providing a single, multi-lumen tube with two or more lumens. A person of ordinary skill in the art will recognize that the pressure sensors 140, 142, valves 154, 156, and other components associated with the conduits could also be similarly associated with a particular lumen in the delivery tube if a multi-lumen tube is used. Further, additional lumens may be provided to separately introduce air or other fluids to the site of the defect 104, including, without limitation, an antibacterial agent, an antiviral agent, a cell-growth promotion agent, an irrigation fluid, or other chemically active agents.

Figure 2C:
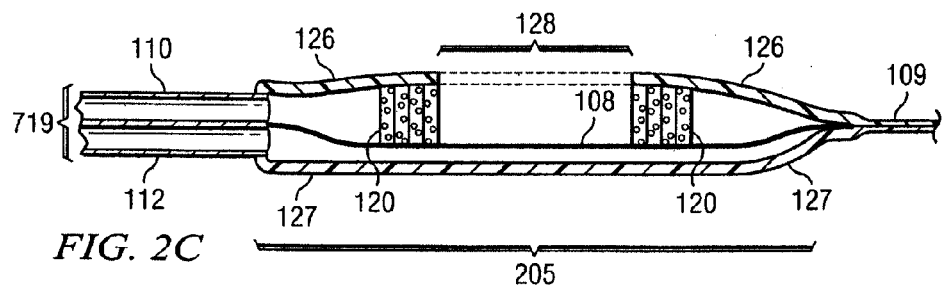
FIG. 2C is a schematic, perspective view of the bladder shown in FIG. 1A without reduced pressure and flattened to be rolled as shown in FIG. 7B.
Figure 7A:
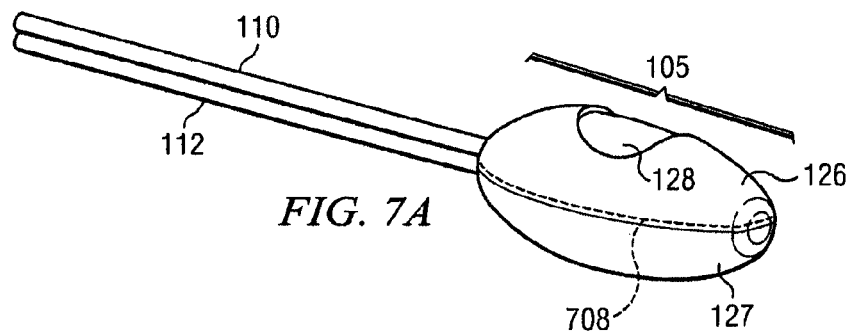
FIG. 7A is a schematic, perspective view of the bladder shown in FIG. 1A.
Figure 7B:
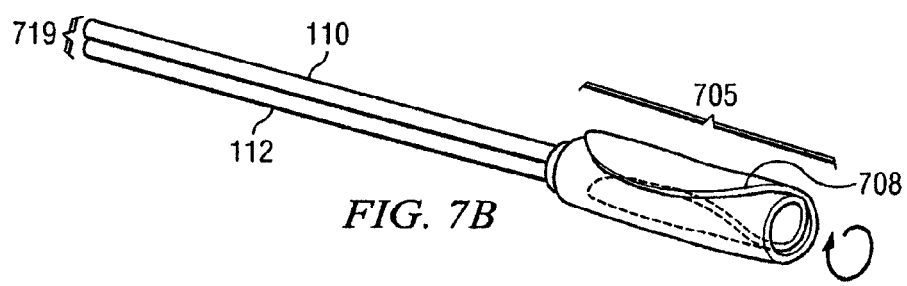
FIG. 7B is a perspective view of the bladder after being rolled or folded.
Figure 7C:
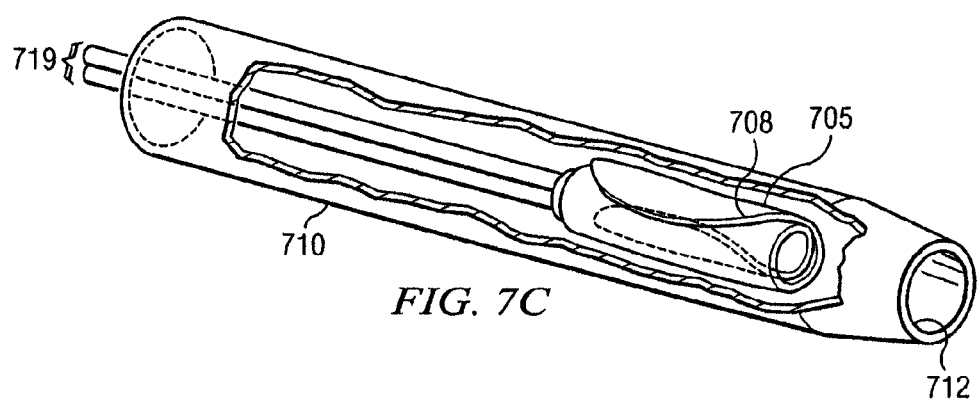
FIG. 7C is a perspective view of the rolled bladder inserted within a delivery catheter.
Figure 8:
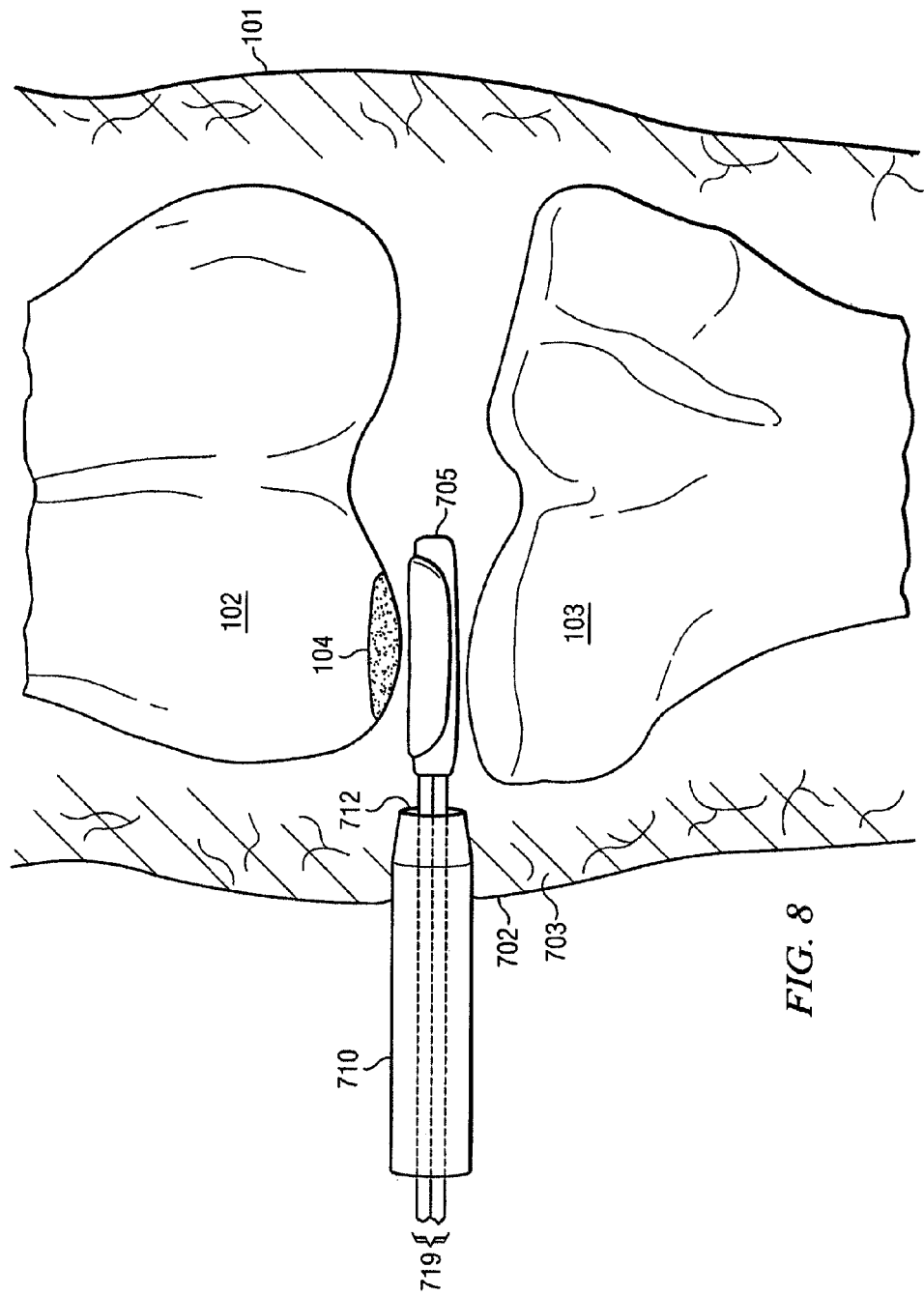
FIG. 8 is a schematic, cross-sectional view of the delivery catheter and rolled bladder of FIG. 7C inserted into the knee joint.

Referring to FIGS. 7A and 2C, the exterior walls 126, 127 of the bladder 105 are flexible as described above. Thus, the bladder 105 may be collapsed or flattened as shown more specifically in FIG. 2C as a flattened bladder 205 and preferably flattened at the edge where the interior wall 108 intersects the exterior walls 126, 127, the edges of which are indicated by the reference number 708 shown by the dashed line in FIG. 7A. The flattened bladder 205 is then folded or rolled as shown in FIG. 7B into a substantially tubular shape as indicated by reference numeral 705. It should be understood again as described above that the reduced-pressure chamber 106 and the bracing chamber 107 (not shown) may not share a common wall such as the interior wall 108, but may have separate walls. The rolled bladder 705 along with the first and second conduits 110, 112 may then be inserted into a delivery catheter 710 as shown in FIG. 7C. The delivery catheter 710 has a distal end 712 that tapers so that the delivery catheter 710 may be surgically or percutaneously inserted in the knee joint between the femur 102 and the tibia 103 to deliver the rolled bladder 705 to the desired lateral site adjacent the defect 104 as shown in FIG. 8. When percutaneously inserted, the delivery catheter 710 may be inserted through a sterile insertion sheath (not shown) that penetrates the skin tissue of the patient. The distal end 712 of the delivery catheter 710 is tapered to assist movement of the delivery catheter 710 through the tissues of the knee joint, but must also have a sufficiently large opening in the tapered distal end 712 to allow the rolled bladder 705 to be pushed out of the delivery catheter 710 and inserted into the knee joint of the patient.

The delivery catheter 710 may be made of any material that provides sufficient strength to allow the delivery catheter 710 to be pushed through the bodily tissues into the knee joint of the patient. Preferably, the materials of the delivery catheter 710 should be bioinert, therefore not causing injury, toxic or immunologic reaction to the surrounding body tissues. Materials of interest includes, but are not limited to, polyimide, polyamide, PBAX™, polyethylene, fluoropolymer, polyurethane, polyisoprene, nylon, steel and the like. It is also contemplated that in one alternate embodiment, the materials of the delivery catheter 710 will allow the delivery catheter 710 an amount of flex. Further, in one embodiment, outer diameter of the delivery catheter 710 is coated with agents to prevent the tube from adhering to the body tissues. For example, the tubing may be coated with heparin, anticoagulants, anti-fibrogens, anti-adherents, anti-thrombinogens or hydrophilic substances. In another embodiment, the outer diameter and/or interior diameter of the delivery catheter 710 are coated with a lubricant agent, including but not limited to, silicone, hydrophilic coating, Surmodics® lubricants, and the like.

Referring again to FIG. 8, the distal end 712 of the delivery catheter 710 is pushed through the skin 702 of the leg 101 of the patient until it is positioned adjacent the knee joint. The first and second conduits 110 and 112, collectively referred to as the conduits 719, may then be manually pushed to force the rolled bladder 705 through the delivery catheter 710 and out of the distal end 712 of the delivery catheter 710 until the rolled bladder 705 is laterally positioned at the desired site adjacent the defect 104. As described above, the femur 102 with the defect 104 may have already undergone microfracture surgery. Although it is understood that exact equipment and method of microfracture surgery may change over time, one of skill in the art readily understands the procedure of microfracture surgery generally includes the medical practitioner, i.e., surgeon or nurse practitioner, who cuts a small incision on the skin 702 exterior to the knee joint. A long thin scope (not shown), for example, an arthroscope, may be inserted through the skin 702 and through the body tissues 703 to the site of the defect 104. If necessary, calcified cartilage is removed. The surgeon may then create microfractures, i.e., small holes, scrapes, tears, in the femur 102 near the defective cartilage, i.e., the defect 104. After the long thin scope is removed, the delivery catheter 710 may be inserted through the same skin opening 702 and body tissue 703 path formed by the scope. In another embodiment, a separate, additional skin opening may be formed for receiving the delivery catheter 710. After the distal end 712 of the delivery catheter 710 is delivered to the surgical site, the conduits 719 may be mechanically or manually pushed so that the rolled bladder 705 moves through and out the distal end 712 of the delivery catheter 710 to be positioned at the desired site adjacent the defect 104.

After the rolled bladder 705 reaches the desired lateral position adjacent the defect 104, the delivery catheter 710 may be removed from the patient's leg 101. The rolled bladder 705 may then be unrolled in the opposite direction shown in FIG. 7B to a relatively flattened shape with the cavity 130 positioned adjacent the defect 104. When the first and second conduits 110, 112 are reconnected to the reduced pressure source 115 and the first fluid supply 111, a positive pressure is applied by the bracing fluid to the bracing chamber 107 so that it expands and exerts a force on the tibia 103 and on the interior wall 108 as described above while at the same time applying a reduced pressure to the reduced-pressure chamber 106 so that the opening 128 in the reduced-pressure chamber 106 (see FIG. 2B) substantially seals the defect 104 as shown in FIG. 1A and described in detail above. The positive pressure applied to the bracing chamber 107 and the weight of the patient being applied by the femur 102 through the manifold structure 120 and the interior wall 108 cause the exterior wall 127 of the bracing chamber 107 to mold to the curvature of the tibia 103 and the surrounding body tissues. Application of the positive pressure to the bracing chamber 107 also forces the interior wall 108 and the manifold structure 120 against the distal end of the femur to force the opening 128 of the reduced-pressure chamber 106 against the defect 104 after which a reduced pressure is applied to the defect 104 via the cavity 130.

As described and shown in FIGS. 1A, 4, and 5 above, the cavity 130 may be filled with the scaffold component 422 or covered by a barrier material 520 closing the opening of the cavity 130. Regardless of the structure, a reduced pressure is ultimately applied via the opening 128 in the reduced-pressure chamber 106 to the defect 104 so that the reduced pressure increases the seepage of blood and bone marrow through the fractures created by the microfracturing surgery to draw blood and other stimulatory agents to the defect site. The reduced pressure therapy or treatment applied to the defect 104 depends on the size and shape of the defect 104 and various other factors known in the art. Consequently, the reduced pressure being applied may be continuous, variable at a specific frequency, or generally cyclical over time depending on the desired treatment for the patient and the characteristics of the defect 104. The opening 128 in the reduced-pressure chamber 106 not only applies the reduced pressure directly to the defect 104, but also mitigates the removal of the sinovial fluid from the knee joint while the reduced pressure is being applied to the defect 104.

Figure 9:
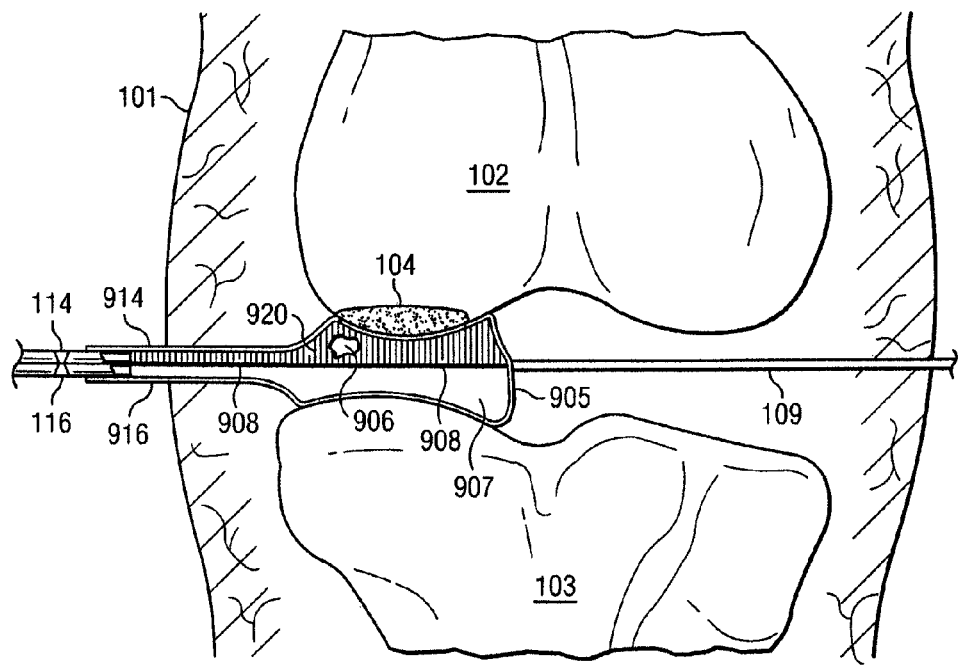
FIG. 9 is a schematic, cross-sectional side view of another embodiment of a bladder similar to the bladder shown in FIG. 1A.

Referring to FIG. 9, another embodiment of a bladder 905 is shown that is substantially similar to the bladder 105 described above including the same components identified with similar reference numerals. The bladder 905 comprises a reduced-pressure chamber 906 and a bracing chamber 907 separated by an interior wall 908, each chamber having an exterior wall 926 and 927, respectively, all as described above with respect to the bladder 105. The reduced-pressure chamber 906 also includes a manifold structure 920 that functions in the same fashion as the manifold structure 420 described above that fills most of the reduced-pressure chamber 906. The reduced-pressure chamber 906 and the bracing chamber 907 each comprise an elongated conduit 914 and 916, respectively, fluidly coupled to each chamber and extending from the bladder 905 through the skin of the leg 101 of the patient. The elongated conduits 914, 916 may be an integrated portion of the reduced-pressure exterior wall 126 and the bracing exterior wall 127, respectively, with the interior wall 908 extending therebetween. The manifold structure 920 extends through and substantially fills the elongated conduit 914 of the reduced-pressure chamber 906. The distal ends of the elongated conduit 914, 916 may be fluidly coupled to the first conduit 110 and the second conduit 112, respectively, for providing a reduced pressure to the reduced-pressure chamber 906 and bracing fluid under a positive pressure to the bracing chamber 907 which function in the same manner as described above. The portion of the manifold structure 920 extending through the elongated conduit 914 of the reduced-pressure chamber 906 provides additional structural support for the reduced pressure chamber 906 so that the bladder 905 can be more easily flattened or rolled as described above to facilitate insertion of the bladder 905 into the delivery catheter 710 (not shown).

Figure 10A:
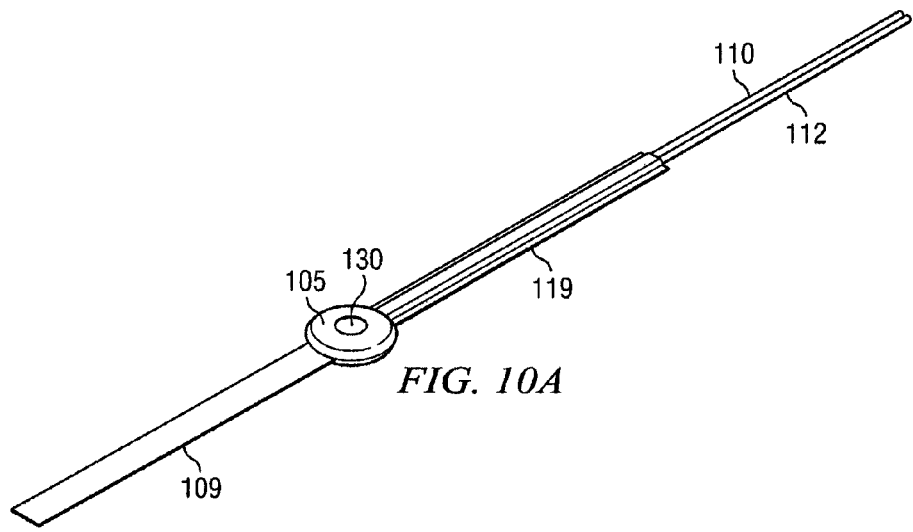
FIGS. 10A and 10B include a perspective and plan views, respectively, of the bladder shown in FIG. 1A including an elongated tab.

Referring to FIG. 10A, a perspective view of the bladder 105 and the first and second conduits 110, 112 is shown. The bladder 105 further comprises an elongated tab 109 extending from the end of the bladder 105 opposite the side that is fluidly coupled to the first and second conduits 110, 112 (see also FIG. 1A). The elongated tab 109 is useful for guiding and manipulating the bladder 105 to the desired lateral position adjacent the defect 104 as described above. More specifically, the arthroscope may be inserted completely through the knee joint to create a path for the elongated tab 109 which would be inserted in advance of the bladder 105 through the delivery catheter 710 and ultimately extend out the other side of the patient's leg 101 as shown in FIG. 1A. The elongated tab 109 may be affixed to the exterior wall 126 of the reduced-pressure chamber 106 to facilitate positioning of the opening 128 in the reduced-pressure chamber 106 adjacent the defect 104. The elongated tab 109 may be affixed to the bladder 105 either prior to being inserted into the knee joint, or at any later point during the surgery to facilitate positioning of the bladder 105. For example, the elongated tab may be inserted from the opposite side of the knee joint through the incisional pathway and into the distal end 712 of the delivery catheter 710 where it can be affixed to or screwed into the bladder 105. The elongated tab 109 then can be used to pull the bladder 105 through the delivery catheter 710 instead of using the first and second conduits 110, 112 to push the bladder 105 to the desired position.

Figure 10B:
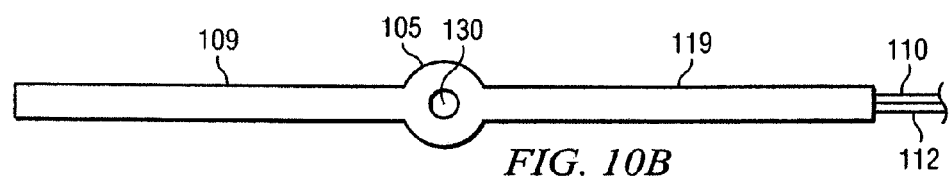

The bladder 105 may also include a sheath 119 covering the first and second conduits 110, 112 and affixed directly to the bladder 105. The sheath 119 may be constructed of a material for providing additional strength to the first and second conduits 110, 112 for pushing the bladder 105 into the desired position adjacent the defect 104 as described above. The sheath 119 and the elongated tab 109 may also be a single continuous piece of material as shown in FIG. 10B to further facilitate pushing and/or pulling the bladder 105 to the desired lateral position adjacent the defect 104 and positioning the opening 128 in the reduced-pressure chamber 106 so that it fully contacts the defect 104.

The design and materials of the bladder chamber, delivery tubes, and the like may be any contemplated in other embodiments of the application and are dependent upon numerous factors, including, for example, the location and size of the tissue site, the pressure of the bracing chamber to maintain the position of the opening 128 in the reduced-pressure chamber 106 against the defect 104. It is contemplated further that for all of the embodiments described herein, the number, size and type of bladder chambers may vary, depending upon the shape of the bone that contains the one or more tissue sites. As such, to better expand the bracing chambers and seal the one or more supportive foam structures to the bone comprising the tissue site, the bladder chamber may have two or more bracing chambers.

The application is also directed to a method of administering a reduced pressure therapy to a tissue site as described above, but more generally according to the following steps. The method comprises performing microfracture surgery on a bone at a tissue site and then delivering an embodiment of the reduced pressure delivery system described above to the tissue site. The method then comprises delivering a bracing substance to the bracing chamber such that the tissue site contact surface is in contact with the tissue site and delivering a reduced pressure to the reduced pressure chamber causing reduced pressure to be applied to the tissue site. This method can be used on any tissue site that is subjected to microfracture surgery. In some embodiments, the tissue site may be located in the knee joint as described above.

In additional embodiments, the application is directed to a method of performing microfracture surgery to a knee. The method comprises creating at least one microfracture in a bone at the base of an articular cartilage defect in the knee, then applying reduced pressure to the site of the defect. The reduced pressure in these embodiments can be applied by any means known in the art, and through any known system capable of delivering reduced pressure to the site. In some embodiments, the reduced pressure is applied using any appropriate embodiment of the reduced pressure delivery system described above.

As various changes could be made in any of the systems, apparatuses and methods described above without departing from the scope of the inventions, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the applicants and no admission is made that any reference constitutes prior art. Applicants reserve the right to challenge the accuracy and pertinence of the cited references.

We claim:

1. A bladder for applying a treatment to a defect in a first bone or a second bone of two bones forming a joint, the bladder comprising:
    a reduced-pressure bladder having an exterior wall forming a reduced-pressure chamber with an interior surface, an opening to the reduced-pressure chamber adapted to substantially surround the defect when positioned against the first bone, and a reduced-pressure port in fluid communication with the reduced pressure chamber for receiving reduced pressure from a source of reduced pressure;
    a manifold disposed within the reduced-pressure chamber and having a surface adapted to form a cavity with a portion of the interior surface when reduced pressure is provided to the reduced-pressure chamber and also providing structural support between the interior surface and the exterior wall to prevent the cavity from collapsing, wherein the reduced-pressure bladder seals the opening around the defect that closes the cavity and is thereby exposed to the reduced pressure within the cavity; and
    a bracing bladder having an exterior wall forming a bracing chamber for receiving a fluid, a first surface of the exterior wall affixed to the reduced-pressure bladder opposite the opening, a second surface of the exterior wall opposing the first surface adapted to be positioned against the second bone, and a port for providing the fluid to the bracing chamber under a positive pressure, the bracing bladder being inflatable with the fluid to provide a cushion between the reduced-pressure bladder and the second bone when the positive pressure is provided to the bracing chamber.

2. The bladder of claim 1, wherein the manifold substantially fills the reduced-pressure chamber and includes a surface exposed through the opening for being positioned adjacent the defect.

3. The bladder of claim 2, wherein the manifold is a foam material in fluid communication with the defect.

4. The bladder of claim 3, wherein the foam material comprises a plurality of open cells having a size ranging from about 100 microns to about 1,500 microns.

5. The bladder of claim 2, wherein the first surface of the bracing bladder forms a common wall between the bracing bladder and the reduced-pressure bladder.

6. The bladder of claim 5, wherein the common wall is substantially inflexible.

7. The bladder of claim 2, wherein the manifold further comprises a scaffold component sized to fill the defect to facilitate tissue formation in the defect.

8. The bladder of claim 7, wherein the scaffold component provides additional support between the first bone and the bracing bladder.

9. The bladder of claim 7, wherein the scaffold component is bioabsorbable.

10. The bladder of claim 9, wherein the scaffold component adheres to the defect.

11. The bladder of claim 7, wherein the scaffold component is coated or infused with growth factors or nutrients.

12. The bladder of claim 1, wherein the reduced pressure bladder and the bracing bladder are comprised of one or more elastomers.

13. The bladder of claim 1, wherein the manifold partially fills the reduced-pressure chamber.

14. The bladder of claim 13, wherein the first surface of the bracing bladder forms a common wall between the bracing bladder and the reduced-pressure bladder.

15. The bladder of claim 14, wherein the common wall is substantially rigid.

16. The bladder of claim 13, further comprising a foam structure positioned in the cavity to provide additional support between the first bone and the bracing bladder.

17. The bladder of claim 16, wherein the foam structure is bioabsorbable.

18. The bladder of claim 16, wherein the foam structure serves as a scaffold for tissue growth.

19. The bladder of claim 18, wherein the foam structure is coated or infused with growth factors or nutrients.

20. The bladder of claim 16, wherein the foam structure adheres to the defect.

21. The bladder of claim 1, further comprising a barrier material covering the opening and closing the cavity, and adapted to directly contact the defect when the reduced-pressure bladder is positioned against the first bone.

22. A bladder for applying a treatment to a defect in a first bone or a second bone of two bones forming a joint, the bladder comprising:
    a reduced-pressure bladder having a reduced-pressure port for fluid communication with a source of reduced pressure and an opening sized to substantially surround the defect in the first bone;
    a bracing bladder having a positive-pressure port for receiving a fluid under a positive pressure and being affixed to the reduced-pressure bladder;
    a manifold disposed within the reduced-pressure bladder and having a surface adapted to form a cavity adjacent the opening for distributing reduced pressure to the defect and providing structural support between the first bone and the bracing bladder to prevent the cavity from collapsing when reduced pressure is provided to the reduced-pressure bladder; and
    wherein the bracing bladder inflates with the fluid when positive pressure is applied to the positive-pressure port to provide a cushion between the manifold and the second bone, and wherein the reduced-pressure bladder seals the opening around the defect that closes the cavity and is thereby exposed to the reduced pressure within the cavity when reduced pressure is provided to the reduced-pressure bladder.

23. The bladder of claim 22, wherein the manifold substantially fills the reduced-pressure bladder and covers the opening in the reduced-pressure bladder whereby the manifold distributes reduced pressure directly to the defect via the opening.

24. The bladder of claim 23, wherein the manifold is a foam material in fluid communication with the defect.

25. The bladder of claim 24, wherein the foam material comprises a plurality of open cells have a size ranging from about 100 microns to about 1,500 microns.

26. The bladder of claim 23, further comprising a common wall between the bracing bladder and the reduced-pressure.

27. The bladder of claim 26, wherein the common wall is substantially inflexible.

28. The bladder of claim 23, wherein the manifold further comprises a scaffold component sized to fill the defect to facilitate tissue formation.

29. The bladder of claim 28, wherein the scaffold component provides additional support between the first bone and the bracing bladder.

30. The bladder of claim 28, wherein the scaffold component is bioabsorbable.

31. The bladder of claim 30, wherein the scaffold component adheres to the defect.

32. The bladder of claim 30, wherein the scaffold component adheres to the manifold.

33. The bladder of claim 28, wherein the scaffold component is coated or infused with growth factors or nutrients.

34. The bladder of claim 22, wherein the reduced pressure bladder and the bracing bladder are comprised of one or more elastomers.

35. The bladder of claim 22, wherein the manifold partially fills the reduced-pressure bladder contacting a portion of the reduced-pressure bladder.

36. The bladder of claim 35, wherein the manifold is a foam material in fluid communication with the defect.

37. The bladder of claim 36, wherein the foam material comprises a plurality of open cells have a size ranging from about 100 microns to about 1,500 microns.

38. The bladder of claim 35, wherein the manifold further comprises a scaffold component sized to fill the defect to facilitate new tissue formation.

39. The bladder of claim 35, further comprising a common wall between the bracing bladder and the reduced-pressure.

40. The bladder of claim 39, wherein the common wall is substantially rigid.

41. The bladder of claim 35, further comprising a foam structure positioned in the cavity to provide additional support between the first bone and the bracing bladder.

42. The bladder of claim 41, wherein the foam structure is bioabsorbable.

43. The bladder of claim 41, wherein the foam structure serves as a scaffold for tissue growth.

44. The bladder of claim 41, wherein the foam material is coated or infused with growth factors or nutrients.

45. The bladder of claim 41, wherein the foam structure adheres to the manifold.

46. The bladder of claim 22, further comprising a barrier material covering the opening and closing the cavity, and adapted to directly contact the defect when the reduced-pressure bladder is positioned against the first bone.

* * * * *